United States Patent [19]
Lewis

[11] Patent Number: 5,288,496
[45] Date of Patent: Feb. 22, 1994

[54] GROWTH PROMOTERS FOR ANIMALS

[75] Inventor: Danny H. Lewis, Hartselle, Ala.

[73] Assignee: Stolle Research & Development Corporation, Decatur, Ala.

[21] Appl. No.: 523,249

[22] Filed: May 15, 1990

[51] Int. Cl.$^5$ ............................................. A61F 13/00
[52] U.S. Cl. ................................. 424/426; 424/422; 424/424; 424/425; 424/486; 424/489; 424/499; 424/502; 604/890.1; 604/891.1
[58] Field of Search ............... 424/426, 425, 424, 422, 424/486; 604/891.1, 892.1

[56] References Cited

U.S. PATENT DOCUMENTS

| | | | |
|---|---|---|---|
| 4,150,108 | 4/1979 | Graham | 424/22 |
| 4,329,332 | 5/1982 | Couvreur et al. | 424/9 |
| 4,389,330 | 6/1983 | Tice et al. | 427/213.36 |
| 4,489,055 | 12/1984 | Couvreur et al. | 424/7.1 |
| 4,530,840 | 7/1985 | Tice et al. | 514/179 |
| 4,542,025 | 9/1985 | Tice et al. | 424/78 |
| 4,675,189 | 6/1987 | Kent | 424/497 |
| 4,677,191 | 6/1987 | Tanaka et al. | 528/361 |
| 4,683,288 | 7/1987 | Tanaka et al. | 528/361 |
| 4,758,935 | 7/1988 | Schaaf | 424/425 |
| 4,874,612 | 10/1989 | Deasy | 424/425 |
| 5,035,891 | 7/1991 | Runkel | 424/422 |

OTHER PUBLICATIONS

Sawyer, G. J., et al., *Australian Veterinary Journal* 65(4): 101-108 (1988).
Ferguson, T. H., et al., *Journal of Controlled Release* 8: 45-54 (1988).
Pitt, C. G., et al., *Journal of Pharmaceutical Sciences* 68(12): 1534-1538 (1979).
Nilsson, C. G., et al., *Am. J. Obstet. Gynecol.* 1229(1): 90-95 (1975).
Dyrmundsson, O. R., in I. Fayez, et al., eds., *New Techniques in Sheep Production* Butterworths, London (1987) pp. 65-76.
Herman, R., *Washington Post*, Health Section Jan. 10, 1989 p. 11.
Beck et al., *Am. J. Obstet. Gynecol.* 147:815-821 (1983).
Beck et al., *Biol. Reprod.* 28:186-195 (1983).
Beck et al., In: *Long-Acting Ster. Contracept.*, ed. Mishell, D. L., Jr., Raven Press, New York (1983), pp. 175-199.
Lewis et al., In: *Male Contraception: Advances and Future Prospects*, ed. Zatuchni, G. I., Harper and Row, Philadelphia (1986), pp. 336-345.
Beck et al., *Am. J. Obstet. Gynecol.* 135:419-426 (1979).
Asch et al., In: *Male Contraception: Advances and Future Prospects*, ed. Zatuchni, G. I., Harper and Row, Philadelphia (1986), pp. 347-360.
Lewis, D. J., In: *Biodegradable Polymers as Drug Delivery Systems*, ed. Chasin, M. et al., Marcel Decker, Inc., New York (1990), pp. 1-41.

Primary Examiner—Gabrielle Phelan
Attorney, Agent, or Firm—Sterne, Kessler, Goldstein & Fox

[57] ABSTRACT

A delivery for providing growth promoters to food animals is provided and a method of promoting growth in food animals using such delivery systems is described.

37 Claims, 1 Drawing Sheet

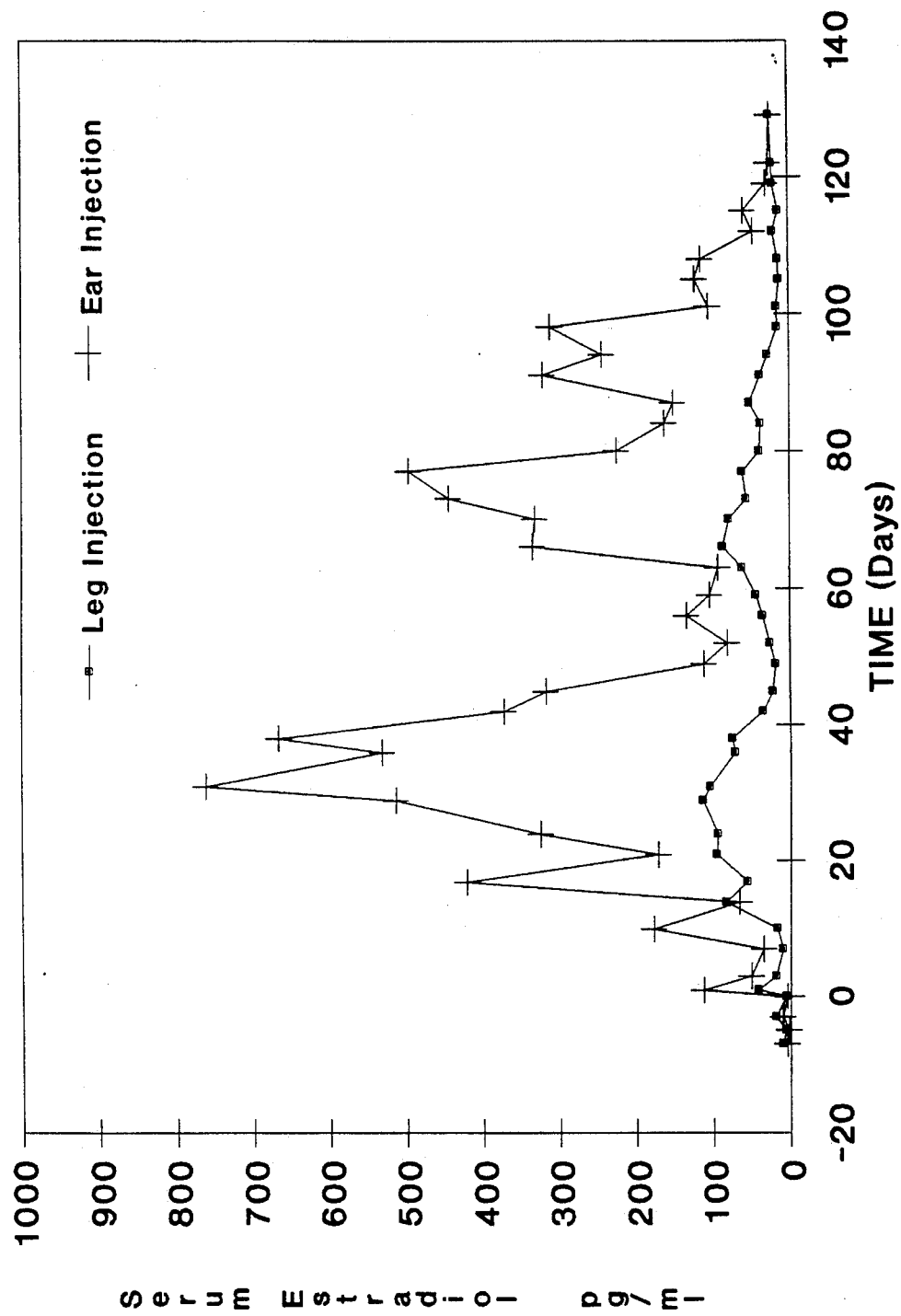

GROWTH PROMOTERS FOR ANIMALS

FIELD OF THE INVENTION

This invention is directed to a delivery system which may be used to provide growth promoters for animals.

BACKGROUND OF THE INVENTION

Recent advances in pharmaceutical bioengineering have stimulated the interest of the food industry in new delivery systems for hormones and other growth promoters.

Steroids, and especially anabolic steroids, are widely used to promote the growth of cattle and other food animals. Such growth promotion is desirable among food producers because it maximizes the weight gain per animal per amount of food consumed.

Currently, steroid products are usually supplied to the animal in the form of a non-biodegradable, implantable steroid time-release pellet which is placed in the ear skin, part of the animal which is discarded upon slaughter. Such delivery systems have been recently reviewed (Sawyer, G.J., et al., Austral. Vet. J. 65:101–108 (1988). The pellet systems cannot provide a pulsed dose of steroid and are often reimplanted two or three times throughout the life of the animal with each implant being administered by a specially designed injector gun.

The use of pellet delivery systems has not met with complete success and they have many disadvantages. The main health concern is that misuse of the non-degradable pellet system may result in harmful levels of such steroids in the meat provided to consumers. Such misuse may arise if the pellet is misplaced. For example, if the pellet is misplaced in the neck or behind the ear instead of in the ear skin, the possibility is raised that the remains of the pellet could be ingested by the consumer. Also, a farmer may mistakenly inject more than one pellet at a time. Also, the pellets are often not successfully implanted and fall to the ground in the treatment pen.

Disadvantages of the currently available pellet implants further include their inability to allow for combination of different drugs with highly controlled release rates in the same unit, and the fact that only 40–70% of the active agent is released. Lastly, commercial implants do not offer a capability in adjusting the duration of action and because of the nondegradable polymeric excipient and the relatively low total surface area of the pellets, it is very difficult to adjust the dosage of the active agent.

Compudose$^R$ is a polymeric controlled release implant device for use with beef cattle which is designed to provide for the continuous delivery of estradiol-17$\beta$ for 200 or 400 days (Ferguson, T. H. et al., J. Cont. Rel 8:45–54 (1988)). The compudose$^R$ implant is made by coating a nonmedicated silicone rubber core with a thin layer of silicone runner which contains micronized crystalline estradiol-17$\beta$. However, the device is not biodegradable.

Biodegradable particles for use in the delivery of steroid hormones have been described (U.S. Pat. No. 4,329,332, U.S. Pat. No. 4,489,055, U.S. Pat. No. 4,683,288, U.S. Pat. No. 4,677,191, U.S. 4,675,189, U.S. Pat. No. 4,530,840, U.S. Pat. No. 4,542,025 and U.S. Pat. No. 4,389,330.

However, none of the above references have suggested or disclosed a method of increasing animal growth by providing a biodegradable microparticle delivery of steroid growth promoters in food animals and a need exists for better, safer delivery systems for steroids in food animals.

SUMMARY OF THE INVENTION

With the above-described needs in mind, the present inventor set out to develop a composition which could be adapted to accomplish the sustained release of steroid growth promoters in food animals in a manner which would not only more efficiently promote the growth of such animals but which would also provide a safer delivery system for the growth promoting compounds.

The invention further provides a method of delivering growth promoters to animals in a multiphasic manner.

The invention further provides a method of delivering two or more active agents at predetermined release rates with the release of each drug being at a different rate and duration by design.

In detail, the invention provides a method of stimulating growth in an animal by treating such animals with injectable, biodegradable microparticles, wherein such microparticles are loaded with at least one growth-promoting steroid. Populations of microparticles with different active steroids or other types of bioactive agents, such as antibiotics or vaccines can be blended to form a composite formulation.

In one embodiment, the growth-promoting steroid is selected from the group consisting of estradiol benzoate, 17$\beta$-estradiol, trenbolone acetate, zeranol, testosterone and testosterone derivatives or combinations thereof.

The invention further concerns the embodiment of the above-described method wherein the biodegradable microparticles comprise a homopolymer or copolymer of lactic/glycolic acid, polycaprolactone, polydioxonone, polyorthoesters, polyanhydides, and natural polymers including albumin, casein, and waxes.

BRIEF DESCRIPTION OF THE DRAWINGS

FIG. 1 graphically presents the data from Table III.

DETAILED DESCRIPTION OF THE PREFERRED EMBODIMENTS

In order to provide a clearer and consistent understanding of the specification and claims, including the scope to be given such terms, the following definitions are provided.

By the term "administered" is intended any method of delivering the growth promoting microparticles of the invention to an animal, such as, for example, parenteral (intravenous, intramuscular, or subcutaneous) administration.

By the term "food animal" is intended any animal that is consumed as a source of protein in the diet of humans or other animals. Typical food animals include bovine animals, for example cattle; ovine animals, for example sheep; porcine, for example pigs; fowl, for example chickens and turkeys; rabbit, and the like.

By "promoting growth" or "increasing growth" is meant increasing the weight or weight gain of an animal by an amount not found in an animal whose growth was not being "promoted."

By "microparticles" is meant solid particles which contain an active agent, herein a growth promoting metabolic steroid, either in solution or in crystalline form. The active agent is dispersed or dissolved within the polymer which serves as the matrix of the particle.

The present invention concerns a method of increasing growth in food animals which comprises providing to such animals biodegradable microparticles loaded with a metabolic steroid. The method of the present invention provides advantages over methods known in the art such as, *inter alia*, an increased weight gain, a biodegradable system, an injectable system which prevents the loss of dose during treatment which often occurs with solid pellet implants, the ability to mix microparticles containing different drugs, the ability to program release (multiphasic release patterns) to give faster rates of drug release as the animal grows larger, and the ability to stimulate growth in poultry.

Further, the method of the invention provides the ability to design a unique blood hormone profile for the animal and a multiphasic hormone delivery system which provides pulsed doses of desired growth promoter, thus eliminating a need for consecutive implant treatments.

The product of the present invention offers the advantage of durations of action ranging from only 30 to 60 days to more than 200 days depending upon the type of microsphere selected. In the preferred embodiment the microspheres are designed to afford growth promotion in animals over a period of 150 to 250 days. The duration of action can be easily controlled by manipulation of the polymer composition, polymer:drug ratio and microsphere size.

Another important advantage of the present invention is that practically all of the active drug is delivered to the animal whereas with existing commercial implants only 40 to 75% of the active agent is released. Because the polymer used in the method of the invention is biodegradable, all of the entrapped drug can be released into the animal.

The preferred construction of microparticles of the invention are described in U.S. Pat. No. 4,389,330, and U.S. Pat. No. 4,530,840, fully incorporated herein by reference. The microparticles of the invention are composed of a polymer which is, preferably, either a homopolymer or copolymer of lactic or glycolic acids. Other biodegradable polymers may be used, such as, for example, polycaprolactone, polydioxonene, polyorthoesters, polyanhydides, and natural polymers including albumin, casein, and waxes.

The present invention is directed to a method of stimulating growth in food animals by administering an injectable, long-acting biodegradable microparticle which contains a growth promoter for food animals. Suitable growth promoters include 17$\beta$-estradiol, estradiol benzoate, trenbolone acetate, zeranol, testosterone, testosterone derivatives (and especially testosterone propionate) and any combination thereof.

In a preferred embodiment, administration of the growth promoter to food animals by the method of the invention is achieved by a single administration of the growth promoter loaded microparticles and the microparticles release the active growth promoter in a constant or pulsed manner into the animal and eliminates the need for repetitive injections.

The formulation of the present invention contains a growth promoter dispersed in a microparticle matrix material. The amount of growth promoter agent incorporated in the microparticles usually ranges from less than 1 wt % to as high as 95 wt. %, preferably 10 to 50 wt. %. By weight % is meant parts of drug per parts of polymer by weight. For example, 10 wt. % would mean 10 parts drug per 90 parts polymer by weight.

The polymeric matrix material of the microparticles present invention must be a biocompatible and biodegradable polymeric material. The term biocompatible is defined as a polymeric material which is not toxic to an animal and not carcinogenic. The matrix material should be biodegradable in the sense that the polymeric material should degrade by bodily processes to products readily disposable by the body and should not accumulate in the body. The biodegraded products also should be biocompatible with the body in the sense that the polymeric matrix is compatible with the body. Suitable examples of polymeric matrix materials include poly (glycolic acid), poly(-d,l-lactic) acid, poly(I -1 actic acid) and copolymers thereof, copolyoxalates, polycaprolactone, poly (lactic acid-caprolactone), and the like. Suitable polymeric materials also include waxes such as glycerol mono- and distearate and casein.

The molecular weight of the polymeric matrix material is of some importance. The molecular weight should be high enough so that it forms satisfactory polymer coatings, i.e., the polymer should be a good film former. Usually, a satisfactory molecular weight is greater than 5,000 daltons. However, since the properties of the film are also partially dependent on the particular polymeric material being used, it is very difficult to specify an appropriate molecular weight range for all polymers. The molecular weight of a polymer is also important from the point of view that molecular weight influences the biodegradation rate of the polymer. For a diffusional mechanism of drug release, the polymer should remain intact until all of the drug is released form the microparticles and then degrade. The drug can also be released from the microparticles as the polymeric excipient bioerodes. By an appropriate selection of polymeric materials a microparticle formulation can be made such that the resulting microparticles exhibit both diffusional release and biodegradation release properties. This is useful in affording multiphasic release patterns.

The microparticle product of the present invention can be prepared by any method which is capable of producing microparticles in a size range acceptable for use in an injectable composition. A preferred method of preparation is the method described in U.S. Pat. No. 4,389,330. In this method the desired growth promoting compound is dissolved or dispersed in an appropriate solvent. To the growth promoting agentcontaining medium is added the polymeric matrix material in an amount relative to the active ingredient which gives a product of the desired loading of active agent. Optionally, all of the ingredients of the microparticle product can be blended in the solvent medium together. Suitable solvents for the growth promoter compound and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like. Preferred solvents for the growth promoter agent are methylene chloride or ethyl acetate.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and most commonly is water although nonaqueous media such as xylene and toluene and synthetic oils and natural oils can be used. Usually, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion can also be formed by adding small drops of the active agent-wall forming material solution to the continuous phase processing medium. The temperature during the formation of the emulsion is not especially critical but can influence the size and quality of the microparticles and the solubility of the drug in the continuous phase. Of course, it is desirable to have as little of the drug in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular active agent being incorporated in the microparticles is adversely affected. Accordingly, the dispersion process can be conducted at any temperature which maintains stable operating conditions, which preferred temperature being about 30° C. to 60° C., depending upon the drug and excipient selected.

The dispersion which is formed is a stable emulsion and from this dispersion the organic solvent immiscible fluid can be partially removed in the first step of the solvent removal process. The solvent can easily be removed by common techniques such as heating, the application of a reduced pressure or a combination of both. The temperature employed to evaporate solvent from the microdroplets is not critical, but should not be that high that it degrades the growth promoting agent employed in the preparation of a given microparticle, nor should it be so high as to evaporate solvent at such a rapid rate to cause defects in the wall forming material. Generally, from 5 to 75 %, preferably 1 to 25% of the solvent is removed in the first solvent removal step.

After the first stage, the dispersed microparticles in the solvent immiscible fluid medium are isolated from the fluid medium by any convenient means of separation. Thus, for example, the fluid can be decanted from the microparticle or the microparticle suspension can be filtered. Still other, various combinations of separation techniques can be used if desired.

Following the isolation of the microparticles from the continuous-phase processing medium, the remainder of the solvent in the microparticles is removed by extraction. In this step, the microparticles can be suspended in the same continuous-phase processing medium used in step one, with or without surfactant, or in another liquid. The extraction medium removes the solvent from the microparticles and yet does not dissolve the microparticles. During the extraction, the extraction medium with dissolved solvent must be removed and replaced with fresh extraction medium. This is best done on a continual basis, where the rate of extraction medium replenishment is critical. If the rate is too slow, agent crystals will protrude from the microparticles or grow in the extraction medium. Obviously, the rate of extraction medium replenishment or a given process is a variable which can easily be determined at the time the process is performed and, therefore, no precise limits for the rate must be predetermined. After the majority of the solvent has been removed from the microparticles, the microparticles are dried by exposure to air or by other conventional drying techniques such as vacuum drying, drying over a desiccant, or the like. This process is very efficient in encapsulating the growth promoting agent since core loadings of up to 80 wt. %, preferably up to 50 wt. % are obtained.

The microparticle product of the present invention is usually made up of particles of a spherical shape although sometimes the microparticles may be irregularly shaped. The microparticles can vary in size, ranging from submicron to millimeter diameters. Preferably, submicron to 250 μm, are desirable for growth promoter formulations allowing administration of the microparticles with a standard gauge needle.

The growth promoting agent bearing microparticles are obtained and stored as a dry material. Prior to administration to an animal or group of animals, the microparticles are suspended in an acceptable pharmaceutical liquid vehicle, and then the suspension is injected into the desired portion of the body of the animal.

The amount of growth promoting agent administered to the animal depends on the particular animal species, growth promoting agent, length of time of treatment, age of the animal and amount of growth promotion which is desired. Since the present invention is concerned with a unique method of promoting growth in food animals by administering growth promoters in a biodegradable microparticle formulation involving encapsulated growth promoting agents, one skilled in the art is well aware of the dosages required to treat a particular animal with a particular growth promoter. Commonly, growth promoters are administered in microgram to milligram amounts, depending upon the size of the animal and the length of treatment time.

The microparticles can be mixed by size or by type so as to provide for a delivery of growth promoters to animals in a multiphasic manner and/or in a manner which provides different growth promoters to the animal at different times, or a mixture of growth promoters to the animal at the same time. Other biologically active agents commonly administered to animals may be blended with the growth promoter formulation. For example, antibiotics, anthelmintics, vaccines, or any desired active agent, either in microparticle form or in conventional, unencapsulated form may be blended with the growth promoter and provided to an animal by the method of the invention.

For example, the method of the invention may also be used to deliver a vaccine containing antigenic material such as an antigen or mixture of antigens of bacterial, viral, or cellular origin. Especially, for example, the method of the invention may be used to deliver *Pasteurella multocide, Pasteurella haemolytica coli, Haemophilus influenzae, Hemophilus ducreyi, Escherichia coli, Salmonella abortus ovis,* and IBR-BVD-PI3 virus antigen(s) and vaccines.

The following examples further describe the materials and methods used in carrying out the invention. The examples are not intended to limit the invention in any manner.

EXAMPLES

Example 1

Preparation of 20%-Loaded Estradiol Benzoate Microparticles

This example describes the preparation of 20% loaded estradiol benzoate microparticles with an 85:15 poly(d,l-estradiol lactide-co-glycolide) (PLGA) excipient.

To prepare a 150 g batch of 20% loaded estradiol benzoate microparticles, 30 g estradiol benzoate is dissolved in 706.06 g of 17% sterile-filtered 85:15 dl-PLGA (MW=135,964)/ethyl acetate solution. During dissolution, the contents of the Erlenmeyer flask are maintained at 60° C. Once the drug has totally dissolved, the drug/polymer solution is added to a 3000-ml jacketed reactor containing 144 g of 3% PVA having been saturated with 183 g of ethyl acetate stirring at 245 rpm at 55° C.

Once the embryonic microparticles have stabilized, the contents of the reaction flask are transferred to 110 liters of water stirring in two 60-liter stainless-steel beakers at 8° C. After having been stirred in the initial wash for 17 minutes, the hardened microparticles are wet sieved onto a 25-micron sieve. The retained product is a transferred to a second water wash of 50 liters stirring in a 60-liter stainless steel beaker at 8° C. After having been in the second wash for 15 minutes, the microparticles are again sieved onto a 25-micron sieve. The retained product is transferred to a third and final wash of 50 liters stirring at 8° C. After stirring in the third wash for about 4 hours, product is isolated by sieving through a sieve stack composed of 25, 45, 90 and 150 micron openings.

Each sieve is washed with liberal portions of fresh water and the product is allowed to air dry.

EXAMPLE 2

Preparation of 15%-Loaded Estradiol Benzoate Microparticles

This example describes the preparation of 15% loaded estradiol benzoate microparticles with poly (d,l-lactide) excipient.

To prepare a 10 g batch of 15%-loaded estradiol benzoate microparticles, 1.5 g estradiol benzoate and 8.6 g dl-PLA, is dissolved in 35.7 g of ethyl acetate in an Erlenmeyer flask at 52° C. The drug/polymer solution is added to a 300-ml jacketed reaction flask containing 196 g of 3% aqueous polyvinyl alcohol having been saturated with 15.6 g of ethyl acetate stirring at 570 rpm at 52° C.

Once the embryonic microparticles have stabilized, the contents of the reaction flask are transferred to 8 liters of water stirring in 10-liter stainless steel beaker at 11° C. After stirring in the initial wash for approximately 4 minutes, the hardened microparticles are wet sieved onto a 25-micron sieve. Retained product is transferred to a second wash of 4 liters stirring at 11° C. After the product has stirred in the second wash for 6 hours, it is isolated by sieving through a sieve stack composed of 25, 45, 90, 150, and 212 micron openings. Each sieve is washed with liberal portions of fresh water to more effectively separate the different sizes of microparticles, and the product is allowed to air dry on sieves overnight.

EXAMPLE 3

Preparation of 17$\beta$-Estradiol Microspheres

A 10-gram batch of 20%-loaded 17$\beta$-estradiol microspheres was prepared by weighing 8g dl-PLA and 2g 17$\beta$-estradiol into a 150 ml Erlenmeyer flask. Then 72g of chloroform was added to 150 ml Erlenmeyer flask. Then 72g of chloroform was added to the flask to dissolve the polymer. After the polymer was completely dissolved, 24g of acetone was added to dissolve the drug. The flask was maintained at 56° C. during the drug/polymer dissolution stage. The solution was added to a 350 ml jacketed resin kettle containing 215g of 5% polyvinyl alcohol stirring at 390 rpm and maintained at 56° C. After 4 minutes, the emulsion had stabilized and the soft microspheres were in the desired size range, the reactor contents were transferred into 8 liters of stirring water at 16° C. The microspheres were then sieved from the wash by a 25-micron sieve and the retained product was transferred into a second 8 liter stirring wash at 16° C. After stirring the product in the second wash for 3 hours, the particles were isolated by sieving through an 8 inch sieve stack composed of 25, 90, and 212 micron mesh. Each sieve was washed with liberal portions of fresh water to effectively separate the different sizes of microspheres. After air drying overnight, the product was collected, weighed and placed under ambient temperature vacuum to dry.

EXAMPLE 4

Preparation of 50%-Loaded Trenbolone Acetate Microparticles

This example describes the preparation of 50%-loaded trenbolone acetate microparticles with an 85:15 poly (d,l-lactide-co-glycolide) excipient.

To prepare a 50 g batch of 50%-loaded trenbolone acetate microparticles, 25 g of trenbolone acetate and 25 g of 85:15 dl-PLGA (MW=135,964), are dissolved in 110 g of ethyl acetate in an Erlenmeyer flask at 52° C. The drug/polymer solution is added to a 1000-ml jacketed reaction flask containing about 400 g of 3% aqueous polyvinyl alcohol having been saturated with 23 g of ethyl acetate stirring at 340 rpm at 52° C.

Once the embryonic microparticles have stabilized, the contents of the reaction flask are transferred to 45 liters of water stirring in a 60-liter stainless steel beaker at 11° C. After having stirred in the initial wash for approximately 10 minutes, the hardened microparticles are wet sieved onto a 25-micron sieve. The product retained by the sieve is transferred to a second wash volume of 40 liters of water stirring at 11° C. After 5 hours stirring in second wash, the microparticles are isolated by sieving through a sieve stack composed of 25, 90, 150, 212 and 500 micron openings. Each sieve is washed with liberal portions of fresh water to more effectively separate the different sizes of microparticles and the product is allowed to air dry on sieves overnight.

EXAMPLE 5

Preparation of 30%-Loaded Trenbolone Acetate Microparticles

This example describes the preparation of 30%-loaded trenbolone acetate microparticles with an 85:15 poly (d,l-lactide-co-glycolide) excipient.

To prepare a 60 g batch of 30%-loaded trenbolone acetate microparticles, 18 g of trenbolone acetate and 42 g of 85:15 dl-PLGA (MW =135,964) are dissolved in 161 g of ethyl acetate in an Erlenmeyer flask at 82° C. The drug/polymer solution is added to a 1000-ml jacketed reaction flask containing about 585 g 3% aqueous polyvinyl alcohol having been saturated with 30 g of ethyl acetate stirring at 300 rpm.

Once the embryonic microparticles have stabilized, the contents of the reaction flask are transferred to 50 liters of water stirring in a 60-liter stainless-steel beaker at 12° C. After having stirred in initial wash for approximately 15 minutes, the hardened microparticles are wet-sieved onto a 25-micron sieve. The product retained by the sieve is transferred to a second wash volume of 40 liters of water stirring at 12° C. After three hours stirring in second wash, the microparticles are isolated by sieving through a sieve stack composed of 25, 90, 150, 212 and 300 micron openings. Each sieve is washed with liberal portions of fresh water to more effectively separate the different sizes of microparticles, and the product is allowed to air-dry on sieves.

EXAMPLE 6

Preparation of 25%-Loaded Zeranol Microparticles

The example describes the preparation of 25%-loaded zeranol microparticles with an 85:15 poly (d,l-lactide-coglycolide) excipient.

To prepare a 5 g batch of 25%-loaded zeranol microparticles, 1.25 g of zeranol and 3.75 g of 85:15 dl-PLGA are dissolved in 33.0 g of ethyl acetate in an Erlenmeyer flask at 59° C. The drug/polymer solution is added to a 100-ml jacketed reaction flask containing about 93 g of 5% aqueous polyvinyl alcohol having been saturated with 5 g of ethyl acetate at 59° C. and stirring at 300 rpm.

Once the embryonic microparticles had stabilized, the contents of the reaction flask are transferred to 3.5 liters of water stirring in a 4-liter beaker at 12° C. After having stirred in the initial wash for approximately ½ hour, the microparticles are wet sieved onto a 25-micron sieve. The retained product is transferred to a second wash of 3.5 liters of water at 12° C. After 3 hours in the second wash the microparticles are isolated by sieving through a sieve stack composed of 25, 45, 90, 150 and 212 micron pore openings. Each sieve is washed with liberal portions of water to more effectively separate the different sizes of microparticles, and the product is allowed to air dry on sieves.

EXAMPLE 7

Preparation of 50%-Loaded Zeranol Microspheres

This example describes the preparation of 50%-loaded zeranol microparticles with a poly (d,l-lactide) excipient.

To prepare a 5 g batch of 50%-loaded zeranol microparticles 2.5 g of zeranol and 2.7 g of dl-PLA, dissolved in 63 g of ethyl acetate in an Erlenmeyer flask at 59° C. The drug/polymer solution is added to a 100 ml jacketed reaction flask containing about 90 g of 3% aqueous polyvinyl alcohol, having been saturated with 6 g of ethyl acetate at 58° C. and stirring at 200 rpm.

Once the embryonic microparticles have stabilized, the contents of the reaction flask are transferred to 4 liters of water stirring in a 4-liter beaker at 12° C. After having stirred in the initial wash for 23 minutes, the microparticles are wet sieved onto a 25-micron sieve. The product retained by the sieve is transferred to a second wash of 4 liters stirring at 90° C. After stirring for three hours in a second wash, the microparticles are isolated by sieving through a sieve stack composed of 25, 45, 90, 150 and 212 micron pore openings. Each sieve is washed with liberal portions of water, and the product is allowed to air dry on sieves.

EXAMPLE 8

Effect of Injectable Microparticle Formulation on Promoting Weight Gain in Beef Cattle Estradiol benzoate microparticles prepared by the methods described above were tested in beef calves to determine the effect on weight gain. Three groups of 22 calves each were used. An untreated control groups, T1, a test group T5, and a positive control group, T6. The test group (T5), received injections of 15 mg of estradiol benzoate microencapsulated in poly(lactide-co-glycolide) excipient. The positive controls (T6) received the commercial implant Ralgro (zeranol active) 36 mg. The Hereford calves weighed less than 250 lbs at the time of treatment and the three groups were comprised of 10 male and 12 female animals per group. All calves remained with their dams during the 168-day study and then they were weaned. Calves were weighted, treatment site inspected, and other general health observations made at 28-day intervals. Animals were weighted on a portable Paul cattle scale equipped with a digital readout. The results of the study are shown in Tables I and II. The biodegradable microparticles were more effective than the commercial implants in increasing the weight of the animals during the treatment period.

TABLE 1

EFFECT OF INJECTABLE MICROPARTICLES ON GROWTH OF HEREFORD BEEF CALVES

| | Daily Gain at Day 140 (lbs) | Gain Over Control | Daily Gain at Day 168 (lbs) | Gain Over Control |
|---|---|---|---|---|
| T1 Untreated Control | 1.66 | — | 1.62 | — |
| T5 Estrogen Microspheres | 1.86 | (12%) | 1.82 | (12.3%) |
| T6 Ralgro | 1.73 | (4.2%) | 1.70 | (4.9%) |
| Estrogen Microparticles vs. Ralgro | | 7.5% increase | | 7.1% increase |

TABLE II

Weight Gain of Hereford Calves Treated with biodegradable microspheres.

| Trt. | Calf I.D. | Sex | Day 0 Wts. 1st | 2nd | Avg. | D28 WT | D56 WT | D84 WT | D112 WT | Day 140 Wts. 1st | 2nd | Avg. | Day 168 Wts. 1st | 2nd | Avg. | Total Gain |
|---|---|---|---|---|---|---|---|---|---|---|---|---|---|---|---|---|
| T5 | 11 | H | 155 | 149 | 152 | 196 | 238 | 312 | 368 | 417 | 418 | 418 | 464 | 468 | 466 | 314 |
| | 24 | H | 159 | 158 | 155 | 189 | 226 | 295 | 338 | 412 | 403 | 488 | 447 | 452 | 458 | 295 |
| | 25 | H | 131 | 124 | 125 | 169 | 216 | 288 | 312 | 399 | 404 | 402 | 459 | 461 | 468 | 333 |

TABLE II-continued

Weight Gain of Hereford Calves Treated with biodegradable microspheres.

| Trt. | Calf I.D. | Sex | Day 0 Wts. 1st | Day 0 Wts. 2nd | Day 0 Wts. Avg. | D28 WT | D56 WT | D84 WT | D112 WT | Day 140 Wts. 1st | Day 140 Wts. 2nd | Day 140 Wts. Avg. | Day 168 Wts. 1st | Day 168 Wts. 2nd | Day 168 Wts. Avg. | Total Gain |
|---|---|---|---|---|---|---|---|---|---|---|---|---|---|---|---|---|
|  | 31 | H | 185 | 178 | 182 | 246 | 258 | 335 | 485 | 492 | 484 | 488 | 536 | 540 | 538 | 357 |
|  | 32 | H | 223 | 216 | 229 | 263 | 312 | 388 | 431 | 588 | 494 | 581 | 545 | 559 | 548 | 328 |
|  | 58 | H | 151 | 144 | 148 | 176 | 214 | 286 | 317 | 399 | 386 | 393 | 428 | 431 | 426 | 278 |
|  | 54 | H | 169 | 172 | 171 | 197 | 235 | 325 | 375 | 452 | 454 | 453 | 499 | 503 | 581 | 331 |
|  | 103 | H | 148 | 148 | 144 | 189 | 236 | 389 | 363 | 467 | 435 | 451 | 475 | 486 | 481 | 337 |
|  | 189 | H | 176 | 169 | 173 | 212 | 258 | 325 | 375 | 454 | 448 | 451 | 493 | 498 | 496 | 323 |
|  | 110 | H | 115 | 189 | 112 | 144 | 179 | 238 | 278 | 325 | 387 | 316 | 366 | 372 | 369 | 257 |
|  | 113 | H | 163 | 161 | 162 | 189 | 237 | 294 | 329 | 398 | 373 | 382 | 418 | 427 | 423 | 261 |
|  | 127 | H | 146 | 141 | 144 | 174 | 284 | 274 | 317 | 384 | 375 | 389 | 428 | 434 | 431 | 288 |
|  | 29 | S | 154 | 158 | 152 | 185 | 214 | 283 | 324 | 421 | 377 | 394 | 435 | 444 | 440 | 288 |
|  | 33 | S | 180 | 173 | 177 | 285 | 256 | 343 | 484 | 491 | 489 | 486 | 526 | 632 | 529 | 353 |
|  | 34 | S | 159 | 144 | 147 | 181 | 226 | 299 | 347 | 433 | 411 | 422 | 459 | 459 | 459 | 312 |
|  | 57 | S | 186 | 168 | 183 | 217 | 255 | 333 | 375 | 462 | 443 | 453 | 594 | 495 | 500 | 317 |
|  | 63 | S | 119 | 115 | 117 | 148 | 180 | 248 | 281 | 375 | 335 | 355 | 389 | 390 | 390 | 273 |
|  | 80 | S | 168 | 165 | 167 | 197 | 237 | 314 | 359 | 434 | 429 | 427 | 486 | 498 | 492 | 326 |
|  | 84 | S | 135 | 131 | 133 | 158 | 180 | 218 | 268 | 322 | 389 | 316 | 360 | 365 | 363 | 230 |
|  | 85 | S | 192 | 195 | 194 | 226 | 268 | 346 | 387 | 479 | 432 | 456 | 584 | 508 | 506 | 313 |
|  | 116 | S | 160 | 147 | 154 | 190 | 224 | 296 | 347 | 433 | 418 | 426 | 467 | 478 | 473 | 319 |
|  | 121 | S | 206 | 196 | 201 | 241 | 279 | 348 | 394 | 462 | 459 | 461 | 508 | 496 | 502 | 301 |
| T6 | 1 | H | 160 | 149 | 155 | 182 | 205 | 273 | 327 | 401 | 396 | 399 | 449 | 442 | 446 | 291 |
|  | 2 | H | 179 | 172 | 176 | 208 | 257 | 329 | 362 | 467 | 436 | 452 | 477 | 486 | 482 | 306 |
|  | 46 | H | 174 | 176 | 175 | 202 | 234 | 305 | 355 | 411 | 414 | 413 | 452 | 455 | 454 | 279 |
|  | 64 | H | 147 | 140 | 144 | 181 | 220 | 286 | 327 | 383 | 373 | 378 | 436 | 426 | 431 | 288 |
|  | 66 | H | 127 | 122 | 125 | 164 | 202 | 274 | 329 | 413 | 391 | 482 | 454 | 460 | 457 | 333 |
|  | 73 | H | 150 | 144 | 147 | 186 | 197 | 262 | 330 | 368 | 344 | 356 | 398 | 395 | 392 | 245 |
|  | 92 | H | 193 | 190 | 192 | 223 | 260 | 333 | 347 | 447 | 433 | 440 | 498 | 493 | 496 | 304 |
|  | 186 | H | 166 | 158 | 162 | 192 | 224 | 252 | 308 | 399 | 357 | 378 | 408 | 416 | 412 | 250 |
|  | 131 | H | 139 | 134 | 137 | 169 | 199 | 264 | 311 | 396 | 361 | 379 | 414 | 396 | 405 | 269 |
|  | 132 | H | 152 | 147 | 150 | 184 | 219 | 299 | 324 | 392 | 394 | 393 | 439 | 419 | 429 | 280 |
|  | 139 | H | 183 | 98 | 181 | 127 | 155 | 215 | 258 | 278 | 276 | 277 | 336 | 326 | 331 | 231 |
|  | 140 | H | 155 | 149 | 152 | 172 | 289 | 272 | 309 | 404 | 378 | 391 | 414 | 403 | 489 | 257 |
|  | 12 | S | 131 | 131 | 131 | 168 | 197 | 257 | 300 | 367 | 355 | 361 | 403 | 415 | 409 | 278 |
|  | 13 | S | 182 | 180 | 181 | 287 | 241 | 305 | 358 | 426 | 412 | 419 | 470 | 477 | 474 | 293 |
|  | 16 | S | 159 | 154 | 157 | 186 | 233 | 299 | 344 | 429 | 422 | 426 | 475 | 478 | 477 | 329 |
|  | 28 | S | 143 | 137 | 140 | M.W. | 197 | 254 | 306 | 486 | 364 | 385 | 429 | 428 | 429 | 289 |
|  | 48 | S | 111 | 107 | 189 | 138 | 167 | 224 | 278 | 378 | 337 | 358 | 480 | 485 | 483 | 294 |
|  | 56 | S | 172 | 163 | 168 | 194 | 220 | 272 | 306 | 382 | 379 | 381 | 422 | 413 | 418 | 250 |
|  | 61 | S | 167 | 164 | 166 | 196 | 238 | 298 | 324 | 389 | 384 | 387 | 434 | 442 | 438 | 273 |
|  | 79 | S | 188 | 188 | 188 | 207 | 247 | 311 | 374 | 468 | 449 | 459 | 516 | 522 | 519 | 331 |
|  | 112 | S | 198 | 188 | 193 | 223 | 265 | 349 | 468 | 492 | 474 | 483 | 542 | 536 | 539 | 346 |
|  | 119 | S | 151 | 144 | 148 | 178 | 212 | 279 | 304 | 418 | 382 | 409 | 424 | 424 | 424 | 277 |
| T1 | 18 | H | 151 | 149 | 150 | 108 | 289 | 270 | 328 | 422 | 394 | 406 | 439 | 443 | 441 | 291 |
|  | 19 | H | 167 | 161 | 164 | 193 | 228 | 289 | 334 | 391 | 385 | 388 | 434 | 411 | 423 | 259 |
|  | 37 | H | 158 | 159 | 159 | 184 | 219 | 292 | 330 | 390 | 388 | 389 | 426 | 413 | 420 | 261 |
|  | 38 | H | 143 | 135 | 139 | 167 | 282 | 278 | 326 | 404 | 417 | 411 | 456 | 442 | 449 | 310 |
|  | 69 | H | 113 | 106 | 110 | 143 | 172 | 232 | 269 | 335 | 327 | 331 | 388 | 388 | 388 | 279 |
|  | 78 | H | 147 | 149 | 148 | 178 | 216 | 288 | 332 | 297 | 398 | 398 | 442 | 445 | 444 | 296 |
|  | 98 | H | 163 | 160 | 162 | 197 | 235 | 297 | 324 | 423 | 391 | 407 | 431 | 423 | 427 | 266 |
|  | 99 | H | 154 | 147 | 151 | 177 | 221 | 279 | 312 | 373 | 377 | 375 | 413 | 418 | 416 | 265 |
|  | 102 | H | 222 | 215 | 219 | 250 | 301 | 386 | 414 | 503 | 500 | 582 | 544 | 544 | 544 | 326 |
|  | 123 | H | 182 | 172 | 177 | 205 | 238 | 306 | 339 | 432 | 390 | 411 | 437 | 446 | 442 | 265 |
|  | 126 | H | 175 | 168 | 172 | 200 | 232 | 307 | 357 | 410 | 413 | 416 | 454 | 442 | 448 | 277 |
|  | 135 | H | 130 | 138 | 130 | 154 | 182 | 241 | 200 | 346 | 346 | 346 | 368 | 384 | 386 | 256 |
|  | 9 | S | 292 | 281 | 282 | 230 | 269 | 335 | 381 | 477 | 443 | 468 | 488 | 588 | 498 | 297 |
|  | 17 | S | 135 | 132 | 134 | 158 | 192 | 251 | 291 | 354 | 368 | 357 | 489 | 487 | 406 | 275 |
|  | 21 | S | 168 | 158 | 163 | 192 | 223 | 294 | 235 | 414 | 318 | 401 | 426 | 434 | 430 | 267 |
|  | 26 | S | 152 | 147 | 158 | 176 | 196 | 252 | 298 | 357 | 352 | 355 | 393 | 394 | 394 | 244 |
|  | 47 | S | 160 | 158 | 159 | 184 | 205 | 277 | 387 | 359 | 265 | 362 | 405 | 408 | 407 | 248 |
|  | 52 | S | 146 | 139 | 143 | M.W. | 189 | 244 | 296 | 358 | 245 | 348 | 397 | 481 | 399 | 257 |
|  | 68 | S | 117 | 114 | 116 | 141 | 168 | 217 | 263 | 341 | 321 | 331 | 389 | 393 | 391 | 276 |
|  | 101 | S | 183 | 180 | 182 | 198 | 235 | 306 | 159 | 413 | 485 | 409 | 455 | 460 | 458 | 276 |
|  | 111 | S | 189 | 182 | 186 | 212 | 241 | 313 | 356 | 438 | 423 | 431 | 472 | 462 | 467 | 282 |
|  | 137 | S | 177 | 169 | 173 | 198 | 219 | 286 | 315 | 412 | 374 | 393 | 403 | 398 | 397 | 224 |

EXAMPLE 9

Duration of Delivery of the Active Agent-Use of a mixture of 20%- and 30%-Loaded Microparticles to Deliver Estradiol Benzoate Two batches, 20% loaded and 30% loaded, of estradiol benzoate microparticles were formulated in an 80/20 blend (by weight and tested) and tested in 6 Holstein bull calves to determine serum estradiol levels. Calves weighing between 92 and 116 pounds at the time of treatment were injected in the ear (3 calves) and in the leg muscle (3 calves) with the test material. A dose of 40 mg of estradiol benzoate (plus slight excess to offset syringe retention) microencapsulated in an 85:15 lactide:glycolide copolymer was given as a 1 cc suspension. The suspending fluid was a 2% aqueous solution of carboxymethyl cellulose with between 20 surfactant. Serum samples were collected for approximately 130 days. The results are shown in Table III, and FIG. 1. These serum estradiol levels correlated well with actual animal weight gain demonstrated when the efficacy of this product was tested in a feed lot trial. This particular combination of steroid and polymeric excipient provided efficacious levels of estradiol in the animals for 168 days.

TABLE III

| | Estradiol Levels | |
|---|---|---|
| Days | SR052-26B Muscle (pg/ml) | SR052-26B Ear (pg/ml) |
| −7 | 10 | 4 |
| −5 | 6 | 2 |
| −3 | 19 | 10 |
| 0 | 6 | 4 |
| 1 | 42 | 113 |
| 3 | 19 | 51 |
| 7 | 10 | 35 |
| 10 | 17 | 178 |
| 14 | 84 | 67 |
| 17 | 56 | 422 |
| 21 | 96 | 172 |
| 24 | 95 | 326 |
| 29 | 114 | 514 |
| 31 | 105 | 762 |
| 36 | 72 | 532 |
| 38 | 75 | 667 |
| 42 | 35 | 373 |
| 45 | 22 | 318 |
| 49 | 19 | 112 |
| 52 | 26 | 81 |
| 56 | 35 | 134 |
| 59 | 44 | 104 |
| 63 | 62 | 93 |
| 66 | 87 | 335 |
| 70 | 79 | 332 |
| 73 | 56 | 445 |
| 77 | 61 | 497 |
| 80 | 39 | 225 |
| 84 | 37 | 163 |
| 87 | 52 | 151 |
| 91 | 38 | 321 |
| 94 | 28 | 244 |
| 98 | 15 | 311 |
| 101 | 16 | 105 |
| 105 | 12 | 122 |
| 108 | 14 | 114 |
| 112 | 20 | 46 |
| 115 | 13 | 58 |
| 119 | 20 | 29 |
| 122 | 21 | 25 |
| 129 | 24 | 24 |

EXAMPLE 10

Duration of Delivery of the Active Agent-Use of a Mixture of 15%- and 30%-Loaded Microparticles to Deliver Estradiol Benzoate Poly(d,l-lactide) was used to microencapsulate estradiol benzoate and the resulting product was administered to 6 Holstein calves to evaluate serum estradiol levels. Two batches, 15% and 30% loaded, were blended to afford the test material. The calves weighing between 101 and 145 pounds, were treated with 40 mg of microencapsulated estradiol benzoate intramuscularly at the base of the ear. The microparticles were suspended in an aqueous carboxymethylcellulose/tween 20 solution. Serum samples were collected at approximately 4-day intervals over a period of several months. The resulting data (Table IV) show that the biodegradable microparticles released the active agent for 200 days in the animals.

TABLE IV

| | Estradiol Levels |
|---|---|
| Day | SR046-120 Ear (pg/ml) |
| −4 | 14.0 |
| 0 | 14.5 |
| 1 | 40.9 |
| 2 | 25.0 |
| 3 | 22.7 |
| 4 | 58.0 |
| 5 | 27.7 |
| 7 | 24.8 |
| 10 | 14.7 |
| 14 | 37.9 |
| 17 | 28.4 |
| 21 | 82.0 |
| 24 | 63.6 |
| 28 | 198.0 |
| 31 | 189.8 |
| 35 | 85.6 |
| 38 | 334.1 |
| 42 | 195.2 |
| 45 | 186.2 |
| 49 | 160.9 |
| 52 | 100.3 |
| 56 | 117.5 |
| 59 | 70.5 |
| 63 | 49.5 |
| 67 | 40.2 |
| 70 | 21.5 |
| 74 | 22.6 |
| 77 | 28.8 |
| 80 | 100.4 |
| 84 | 10.3 |
| 87 | 28.0 |
| 91 | 18.6 |
| 94 | 47.8 |
| 98 | 33.2 |
| 101 | 32.6 |
| 105 | 57.7 |
| 108 | 71.3 |
| 112 | 88.9 |
| 115 | 91.5 |
| 119 | 109.0 |
| 122 | 189.7 |
| 126 | 132.6 |
| 129 | 352.5 |
| 133 | 366.4 |
| 136 | 106.1 |
| 140 | 105.7 |
| 143 | 107.4 |
| 147 | 126.7 |
| 150 | 92.7 |
| 154 | 118.9 |
| 157 | 100.3 |
| 161 | 69.5 |
| 168 | 58.9 |
| 175 | 34.8 |
| 182 | 51.0 |
| 189 | 22.9 |
| 196 | 19.1 |
| 203 | 16.5 |

EXAMPLE 11

Duration of Delivery of the Active Agent-Use of a Mixture of 30%- and 50%-Loaded Microparticles to Deliver Trenbolone Acetate Trenbolone acetate was microencapsulated in an 85:15 copolymer of lactic and glycolic acids, and the resulting product evaluated in 6 Holstein bull calves. The formulation tested was a 50/50 blend of a 30% loaded batch and a 50% loaded batch. Calves weighing between 91 and 117 pounds were injected either i.m. in the leg (3 calves) or at the base of the ear (3 calves) with 200 mg of encapsulated trenbolone acetate. The microparticles were suspended in an aqueous carboxymethylcellulose/tween 20 injection vehicle. Serum samples were collected and analyzed for trenbolone acetate at selected intervals. Table V shows that elevated serum drug levels were achieved over the 150-day test period. This formulation was shown to be efficacious in increasing the weight gain of beef calves.

TABLE V

| Days | Trenbolone acetate levels | |
|---|---|---|
| | SR046-100 Ear (pg/ml) | SR046-100 Muscle (pg/ml) |
| −4 | 39 | 13 |
| −1 | 13 | 24 |
| 0 | 26 | 47 |
| 1 | 300 | 183 |
| 2 | 202 | 104 |
| 3 | 269 | 91 |
| 4 | 233 | 135 |
| 5 | 290 | 124 |
| 7 | 295 | 147 |
| 10 | 156 | 128 |
| 14 | 146 | 92 |
| 17 | 300 | 91 |
| 21 | 272 | 88 |
| 28 | 130 | 30 |
| 31 | 141 | 94 |
| 35 | 318 | 43 |
| 38 | 285 | 150 |
| 42 | 219 | 222 |
| 45 | 466 | 295 |
| 49 | 517 | 231 |
| 52 | 349 | 128 |
| 56 | 273 | 129 |
| 59 | 77 | 120 |
| 63 | 83 | 86 |
| 66 | 268 | 77 |
| 70 | 106 | 81 |
| 73 | 66 | 49 |
| 77 | 206 | 113 |
| 80 | 130 | 111 |
| 84 | 151 | 125 |
| 87 | 113 | 107 |
| 91 | 105 | 84 |
| 94 | 68 | 101 |
| 98 | 61 | 65 |
| 101 | 89 | 69 |
| 105 | 108 | 57 |
| 108 | 46 | 90 |
| 112 | 103 | 79 |
| 115 | 140 | 83 |
| 119 | 115 | 68 |
| 122 | 97 | 122 |
| 129 | 18 | 122 |
| 136 | 53 | 78 |
| 143 | 35 | 73 |
| 150 | 35 | 50 |

Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, and wherein the polymeric matrix of said microparticle composition is selected from the group consisting of poly-d,l-lactic acid, poly-L-lactic acid, polyglycolic acid, copolymers of mixed d,l-lactic acid and glycolic acid, copolymers of L-lactic acid and glycolic acid, copolyoxalates, polycaprolactone, poly(lactic acid-caprolactone), poly(glycolic acid-caprolactone), casein, albumin, and waxes.

2. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, and wherein said microparticles are loaded with 1 to 75 wt.% of said growth promoter based on the weight of said polymeric matrix.

3. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, and wherein said microparticles range in size from 1 to 250 microns.

4. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, wherein said microparticle composition is in a liquid injection vehicle, and wherein said liquid injection vehicle is selected from the group consisting of physiological saline solution, and an aqueous solution of carboxymethyl cellulose with a surfactant.

5. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, and wherein said microparticles are administered by intramuscular injection.

6. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, and wherein a combination of two or more separately microencapsulated growth promoters is administered.

7. A method of promoting growth in animals wherein said method comprises administration, in amounts sufficient to promote growth in said animals, of an injectable, biodegradable, composition comprising microparticles, wherein said microparticles comprise a steroid growth promoter within a polymeric matrix, and wherein two or more growth promoters are incorporated within a single microparticle matrix.

8. The method of any of claims 1-5, wherein said microparticles are administered by subcutaneous injection.

9. The method of any of claims 1-5, wherein the growth promoter is selected from the group consisting of estradiol benzoate, trenbolone acetate, zeranol and 17β-estradiol.

10. The method of claim 9, wherein said growth promoter is estradiol benzoate.

11. The method of claim 9, wherein said growth promoter is trenbolone acetate.

12. The method of claim 9, wherein said growth promoter is zeranol.

13. The method of claim 9, wherein said growth promoter is 17β-estradiol.

14. The method of claim 6 wherein said growth promoters are selected from the group consisting of 17β-estradiol, estradiol benzoate, trenbolone acetate, zeranol and testosterone.

15. The method of claim 14 wherein said combination comprises any two of the growth promoters of claim 14.

16. The method of claim 15 wherein said combination comprises zeranol and estradiol benzoate.

17. The method of claim 15 wherein said combination comprises zeranol and 17β-estradiol.

18. The method of claim 15 wherein said combination comprises zeranol and testosterone.

19. The method of claim 15 wherein said combination comprises trenbolone acetate and estradiol benzoate.

20. The method of claim 15 wherein said combination comprises trenbolone acetate and 17β-estradiol.

21. The method of claim 15 wherein said combination comprises 17β-estradiol and estradiol benzoate.

22. The method of claim 15 wherein said combination comprises 17β-estradiol and testosterone.

23. The method of claim 15 wherein said combination comprises estradiol benzoate and testosterone.

24. The method of claim 15 wherein said combination comprise testosterone and trenbolone acetate.

25. The method of claim 15 wherein said combination comprises zeranol and trenbolone acetate.

26. The method of claim 7 wherein said growth promoters are selected from the group consisting of zeranol, trenbolone acetate, estradiol benzoate, 17β-estradiol and testosterone.

27. The method of claim 26 wherein said combination comprise any two of the growth promoters of claim 26.

28. The method of claim 27 wherein said combination comprises zeranol and estradiol benzoate.

29. The method of claim 27 wherein said combination comprises zeranol and 17β-estradiol.

30. The method of claim 27 wherein said combination comprise zeranol and testosterone.

31. The method of claim 27 wherein said combination comprises trenbolone acetate and estradiol benzoate.

32. The method of claim 27 wherein said combination comprises trenbolone acetate and 17β-estradiol.

33. The method of claim 27 wherein said combination comprises 17β-estradiol and estradiol benzoate.

34. The method of claim 27 wherein said combination comprises 17β-estradiol and testosterone.

35. The method of claim 27 wherein said combination comprises estradiol benzoate and testosterone.

36. The method of claim 27 wherein said combination comrpises testosterone and trenbolone acetate.

37. The method of claim 27 wherein said combination comprises zeranol and trenbolone acetate.

* * * * *

UNITED STATES PATENT AND TRADEMARK OFFICE
CERTIFICATE OF CORRECTION

PATENT NO. : 5,288,496

DATED : Feb. 22, 1994

INVENTOR(S) : Danny H. Lewis

It is certified that error appears in the above-indentified patent and that said Letters Patent is hereby corrected as shown below:

On the title page, item [56]:

| | |
|---|---|
| Under "U.S. Patent Documents": | "4,758,935" should read --4,758,435-- |
| Under "Other Publications": | "Nilsson, C.G., et al., Am. J. Obstet. Gynecol. 1229(1):90-95 (1975)" should read --Nilsson, C.G., et al., Am. J. Obstet. Gynecol. 122(1):90-95 (1975)-- |
| Under "Abstract" line 1 | please add the word --system-- between the words "delivery" and "for" |

| Column | Line | |
|---|---|---|
| 4 | 15 | "poly(I -lactic acid)" should read --poly(l-lactic acid)-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 4 | 34 | "form" should read --from-- |
| 4 | 49 | "agentcontaining" should read --agent-containing-- |
| 7 | 9 | please delete the word "estradiol" |
| 8 | 6 | "Sg" should read --8g-- |
| 9 | 28 | "coglycolide" should read --co-glycolide-- |
| 10 | 22 | "groups" should read --group-- |
| 10 | 66 | Please delete "T5" in column 1 of Table II |
| 10 | 66 | Column 10 of Table II; "368" should read --360-- |
| 10 | 67 | Column 5 of Table II; "158" should read --150-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 10 | 67 | Column 8 of Table II; "226" should read --220-- |
| 10 | 67 | Column 10 of Table II; "338" should read --330-- |
| 10 | 67 | Column 13 of Table II; "488" should read --408-- |
| 10 | 67 | Column 16 of Table II; "458" should read --450-- |
| 10 | 68 | Column 6 of Table II; "125" should read --128-- |
| 10 | 68 | Column 16 of Table II; "468" should read --460-- |
| 11 | 5 | Column 7 of Table II; "246" should read --208-- |
| 11 | 5 | Column 10 of Table II; "485" should read --405-- |

UNITED STATES PATENT AND TRADEMARK OFFICE
CERTIFICATE OF CORRECTION

PATENT NO.   : 5,288,496
DATED        : Feb. 22, 1994
INVENTOR(S)  : Danny H. Lewis It is certified that error appears in the above-indentified patent and that said Letters Patent is hereby corrected as shown below:

| Column | Line | |
|---|---|---|
| 11 | 6 | Column 6 of Table II;  "229" should read --220-- |
| 11 | 6 | Column 11 of Table II;  "588" should read --508-- |
| 11 | 6 | Column 13 of Table II;  "581" should read --501-- |
| 11 | 6 | Column 15 of Table II;  "559" should read --550-- |
| 11 | 7 | Column 2 of Table II;  "58" should read --50-- |
| 11 | 7 | Column 14 of Table II;  "428" should read --420-- |
| 11 | 8 | Column 16 of Table II;  "581" should read --501-- |
| 11 | 9 | Column 5 of Table II;  "148" should read --140-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|--------|------|---|
| 11 | 9 | Column 9 of Table II; "389" should read --309-- |
| 11 | 10 | Column 2 of Table II; "189" should read --109-- |
| 11 | 10 | Column 8 of Table II; "258" should read --250-- |
| 11 | 11 | Column 5 of Table II; "189" should read --109-- |
| 11 | 11 | Column 9 of Table II; "238" should read --230-- |
| 11 | 11 | Column 10 of Table II; "278" should read --270-- |
| 11 | 11 | Column 12 of Table II; "387" should read --307-- |
| 11 | 12 | Column 1 of Table II; please insert --T5-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

Page 6 of 16

It is certified that error appears in the above-indentified patent and that said Letters Patent is hereby corrected as shown below:

| Column | Line | |
|---|---|---|
| 11 | 12 | Column 8 of Table II; "237" should read --230-- |
| 11 | 12 | Column 11 of Table II; "398" should read --390-- |
| 11 | 13 | Column 8 of Table II; "284" should read --204-- |
| 11 | 13 | Column 13 of Table II; "389" should read --380-- |
| 11 | 14 | Column 5 of Table II; "158" should read --150-- |
| 11 | 14 | Column 13 of Table II; "394" should read --399-- |
| 11 | 15 | Column 7 of Table II; "285" should read --205-- |
| 11 | 15 | Column 10 of Table II; "484" should read --404-- |

UNITED STATES PATENT AND TRADEMARK OFFICE
CERTIFICATE OF CORRECTION

PATENT NO.  : 5,288,496
DATED       : Feb. 22, 1994
INVENTOR(S) : Danny H. Lewis It is certified that error appears in the above-indentified patent and that said Letters Patent is hereby corrected as shown below:

| Column | Line | |
|---|---|---|
| 11 | 15 | Column 12 of Table II; "489" should read --480-- |
| 11 | 15 | Column 15 of Table II; "632" should read --532-- |
| 11 | 16 | Column 4 of Table II; "159" should read --150-- |
| 11 | 17 | Column 5 of Table II; "168" should read --180-- |
| 11 | 17 | Column 14 of Table II; "594" should read --504-- |
| 11 | 19 | Column 12 of Table II; "429" should read --420-- |
| 11 | 20 | Column 10 of Table II; "268" should read --260-- |
| 11 | 20 | Column 12 of Table II; "389" should read --309-- |

UNITED STATES PATENT AND TRADEMARK OFFICE
CERTIFICATE OF CORRECTION

PATENT NO. : 5,288,496                    Page 8 of 16
DATED      : Feb. 22, 1994
INVENTOR(S) : Danny H. Lewis It is certified that error appears in the above-indentified patent and that said Letters Patent is hereby corrected as shown below:

| Column | Line | |
|--------|------|---|
| 11 | 21 | Column 14 of Table II; "584" should read --504-- |
| 11 | 24 | Column 1 of Table II; please insert "T6" |
| 11 | 28 | Column 13 of Table II; "482" should read --402-- |
| 11 | 29 | Column 15 of Table II; "395" should read --385-- |
| 11 | 31 | Column 2 of Table II; "186" should read --106-- |
| 11 | 34 | Column 1 of Table II; please insert --T6-- |
| 11 | 34 | Column 4 of Table II; "183" should read --103-- |
| 11 | 34 | Column 6 of Table II; "181" should read --101-- |
| 11 | 35 | Column 8 of Table II; "289" should read --209-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 11 | 35 | Column 16 of Table II; "489" should read --409-- |
| 11 | 36 | Column 7 of Table II; "168" should read --160-- |
| 11 | 37 | Column 7 of Table II; "287" should read --207-- |
| 11 | 37 | Column 10 of Table II; "358" should read --350-- |
| 11 | 38 | Column 17 of Table II; "329" should read --320-- |
| 11 | 39 | Column 7 of Table II; "M.W." should read --N.W.-- |
| 11 | 39 | Column 11 of Table II; "486" should read --406-- |
| 11 | 40 | Column 2 of Table II; "48" should read --40-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 11 | 40 | Column 6 of Table II; "189" should read --109-- |
| 11 | 40 | Column 10 of Table II; "278" should read --270-- |
| 11 | 40 | Column 14 of Table II; "480" should read --400-- |
| 11 | 40 | Column 15 of Table II; "485" should read --405-- |
| 11 | 40 | Column 16 of Table II; "483" should read --403-- |
| 11 | 41 | Column 10 of Table II; "306" should read --308-- |
| 11 | 42 | Column 8 of Table II; "238" should read --230-- |
| 11 | 43 | Column 2 of Table II; "79" should read --70-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 11 | 44 | Column 10 of Table II; "468" should read --408-- |
| 11 | 45 | Column 10 of Table II; "304" should read --306-- |
| 11 | 45 | Column 13 of Table II; "409" should read --400-- |
| 11 | 46 | Column 1 of Table II; "T1" |
| | | Column 7 of Table II; "108" should read --180-- |
| 11 | 46 | Column 8 of Table II; "289" should read --209-- |
| 11 | 46 | Column 13 of Table II; "406" should read --408-- |
| 11 | 49 | Column 8 of Table II; "282" should read --202-- |

UNITED STATES PATENT AND TRADEMARK OFFICE
CERTIFICATE OF CORRECTION

Page 12 of 16

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 11 | 51 | Column 11 of Table II; "297" should read --397-- |
| 11 | 54 | Column 9 of Table II; "386" should read --388-- |
| 11 | 54 | Column 13 of Table II; "582" should read --502-- |
| 11 | 55 | Column 9 of Table II; "306" should read --300-- |
| 11 | 56 | Column 11 of Table II; "410" should read --418-- |
| 11 | 57 | Column 5 of Table II; "138" should read --130-- |
| 11 | 57 | Column 10 of Table II; "200" should read --280-- |
| 11 | 57 | Column 14 of Table II; "368" should read --388-- |

UNITED STATES PATENT AND TRADEMARK OFFICE
CERTIFICATE OF CORRECTION

PATENT NO. : 5,288,496

DATED : Feb. 22, 1994

INVENTOR(S) : Danny H. Lewis

It is certified that error appears in the above-indentified patent and that said Letters Patent is hereby corrected as shown below:

| Column | Line | |
|---|---|---|
| 11 | 58 | Column 4 of Table II; "292" should read --202-- |
| 11 | 68 | Column 5 of Table II; "281" should read --201-- |
| 11 | 58 | Column 6 of Table II; "282" should read --202-- |
| 11 | 58 | Column 13 of Table II; "468" should read --460-- |
| 11 | 58 | Column 15 of Table II; "588" should read --508-- |
| 11 | 59 | Column 12 of Table II; "368" should read --360-- |
| 11 | 59 | Column 14 of Table II; "489" should read --409-- |
| 11 | 59 | Column 15 of Table II; "487" should read --407-- |

UNITED STATES PATENT AND TRADEMARK OFFICE
CERTIFICATE OF CORRECTION

Page 14 of 16

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 11 | 59 | Column 16 of Table II; "406" should read --408-- |
| 11 | 60 | Column 10 of Table II; "235" should read --335-- |
| 11 | 60 | Column 12 of Table II; "318" should read --388-- |
| 11 | 61 | Column 10 of Table II; "298" should read --290-- |
| 11 | 62 | Column 10 of Table II; "387" should read --307-- |
| 11 | 62 | Column 12 of Table II; "265" should read --365-- |
| 11 | 63 | Column 7 of Table II; "M.W." should read --N.W.-- |
| 11 | 63 | Column 11 of Table II; "358" should read --350-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 11 | 63 | Column 12 of Table II; "245" should read --345-- |
| 11 | 63 | Column 15 of Table II; "481" should read --401-- |
| 11 | 64 | Column 8 of Table II; "168" should read --160-- |
| 11 | 65 | Column 10 of Table II; "159" should read --359-- |
| 11 | 65 | Column 12 of Table II; "485" should read --405-- |
| 11 | 67 | Column 15 of Table II; "398" should read --390-- |
| 12 | 63 | "between 20" should read --1% tween 20-- |
| 14 | 61 | "tactic" should read --lactic-- |

UNITED STATES PATENT AND TRADEMARK OFFICE
CERTIFICATE OF CORRECTION

PATENT NO. : 5,288,496
DATED : Feb. 22, 1994
INVENTOR(S) : Danny H. Lewis

It is certified that error appears in the above-indentified patent and that said Letters Patent is hereby corrected as shown below:

| Column | Line | |
|---|---|---|
| 15 | 24 | Please insert into column 1 of Table V "24" |
| 15 | 24 | Please insert into column 2 of Table V "145" |
| 15 | 24 | Please insert into column 3 of Table V "62" |

Signed and Sealed this

Eleventh Day of July, 1995

Attest:

BRUCE LEHMAN

Attesting Officer   Commissioner of Patents and Trademarks

UNITED STATES PATENT AND TRADEMARK OFFICE
CERTIFICATE OF CORRECTION

PATENT NO. : 5,288,496

DATED : Feb. 22, 1994

INVENTOR(S) : Danny H. Lewis

It is certified that error appears in the above-identified patent and that said Letters Patent is hereby corrected as shown below:

On title page, item [73], "Decatur, Ala." should read --Cincinnati, Ohio--
Column 6, line 61, delete the word "coli"

Signed and Sealed this

Thirteenth Day of February, 1996

*Attest:*

BRUCE LEHMAN

*Attesting Officer*  *Commissioner of Patents and Trademarks*